US010203271B1

(12) United States Patent
McCaffrey

(10) Patent No.: US 10,203,271 B1
(45) Date of Patent: Feb. 12, 2019

(54) PARTICLE INTERACTION CHARACTERIZATION USING OVERLAPPING SCATTERING AND CONCENTRATION MEASUREMENTS

(71) Applicant: John McCaffrey, Columbia, MD (US)

(72) Inventor: John McCaffrey, Columbia, MD (US)

(73) Assignee: Malvern Panalytical Limited, Malvern (GB)

(*) Notice: Subject to any disclaimer, the term of this patent is extended or adjusted under 35 U.S.C. 154(b) by 0 days.

(21) Appl. No.: 15/201,542

(22) Filed: Jul. 4, 2016

Related U.S. Application Data

(60) Provisional application No. 62/189,194, filed on Jul. 6, 2015.

(51) Int. Cl.
*G01N 15/02* (2006.01)
*G01J 1/42* (2006.01)
*G01N 21/53* (2006.01)
*G01N 15/00* (2006.01)

(52) U.S. Cl.
CPC .......... *G01N 15/0211* (2013.01); *G01J 1/429* (2013.01); *G01N 21/53* (2013.01); *G01N 2015/0065* (2013.01); *G01N 2201/062* (2013.01); *G01N 2201/08* (2013.01); *G01N 2201/121* (2013.01)

(58) Field of Classification Search
CPC .................. G01N 15/0211; G01N 33/5044
See application file for complete search history.

(56) References Cited

U.S. PATENT DOCUMENTS

| 5,279,146 A * | 1/1994 | Asano | G01N 21/3504 422/83 |
| 5,760,900 A * | 6/1998 | Ito | G01N 15/1434 250/461.2 |
| 6,413,786 B1 * | 7/2002 | Hansen | C12Q 1/6816 356/128 |
| 6,944,322 B2 * | 9/2005 | Johnson | G01N 15/14 382/128 |
| 2004/0246480 A1 * | 12/2004 | Hansen | G01N 33/585 356/336 |
| 2006/0274309 A1 * | 12/2006 | Cerni | G01N 15/1459 356/338 |
| 2009/0251696 A1 * | 10/2009 | McNeil-Watson | G01N 15/1427 356/336 |

(Continued)

*Primary Examiner* — David Porta
*Assistant Examiner* — Djura Malevic
(74) *Attorney, Agent, or Firm* — Kristofer E. Elbing

(57) ABSTRACT

Disclosed in one general aspect is a particle interaction characterization instrument that comprises a flow cell for a liquid sample that includes suspended particles and a light source positioned to illuminate the suspended particles in the liquid sample fluid in the sample vessel. A first scattering detector is positioned to receive light from the light source that has been scattered by the particles suspended in sample fluid in the sample vessel at at least one predetermined scattering angle. An ultraviolet transmittance detector is positioned to receive a portion of the light from the source that passes through the suspended particles without being absorbed or scattered. Interaction analysis logic is responsive to both the scattering detector and the ultraviolet detector, and is operative to derive at least one interaction property for the suspended particles.

13 Claims, 2 Drawing Sheets

(56) References Cited

U.S. PATENT DOCUMENTS

2010/0021878 A1* 1/2010 Kim .................... G01N 15/147
                                                        435/2
2016/0252453 A1* 9/2016 Lewis ................ G01N 21/4133
                                                        356/51
2016/0258876 A1* 9/2016 Al Hosani ................ G01J 3/42

* cited by examiner

PARTICLE INTERACTION CHARACTERIZATION USING OVERLAPPING SCATTERING AND CONCENTRATION MEASUREMENTS

FIELD OF THE INVENTION

This invention relates to methods and apparatus for detecting particle interaction characteristics, such as $B_{22}$ and $K_D$ interaction parameters.

BACKGROUND OF THE INVENTION

Measuring molecular self-interaction can help to indicate whether particular particles will aggregate or crystallize. One measure of self-interaction is the $B_{22}$ interaction parameter. Prior art methods of detecting the $B_{22}$ interaction parameter are described in U.S. Pat. No. 7,630,076 and US Appl. No. 20070291265, which are herein incorporated by reference. As shown in FIG. 1, these methods involve performing scattering and ultraviolet (UV) absorbance measurements on a sample in a flow cell.

SUMMARY OF THE INVENTION

Several aspects of this invention are presented in this specification and its claims. Systems according to the invention can simplify the measurement of interaction parameters by allowing them to be performed with a simpler instrument. This is particularly advantageous in that simultaneous UV and scattering measurements can be performed without requiring alignment of two sources and the uncertainty that can arise from potential misalignment. Systems according to the invention can also operate without optical fibers in the incoming optical path, which can eliminate solarization effects.

DETAILED DESCRIPTION OF AN ILLUSTRATIVE EMBODIMENT

Figure 1:
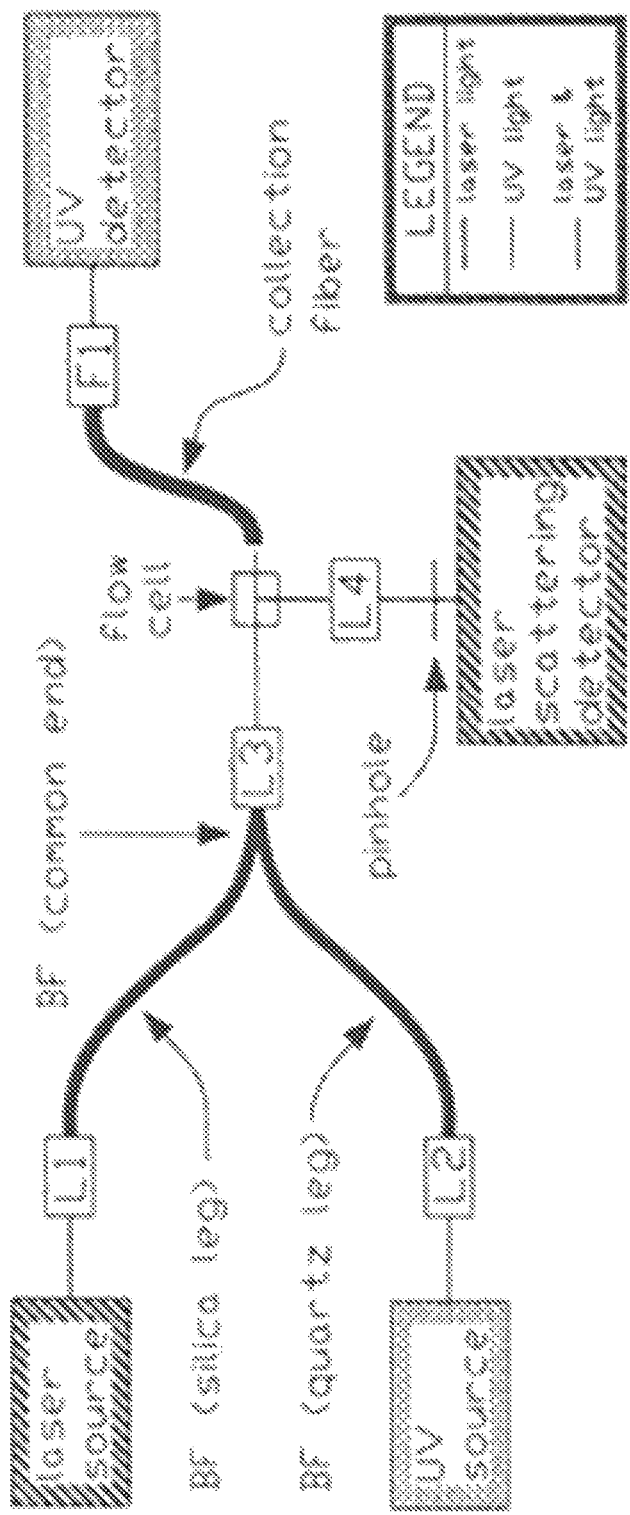
FIG. 1 is a block diagram of a prior art instrument.
Figure 2:
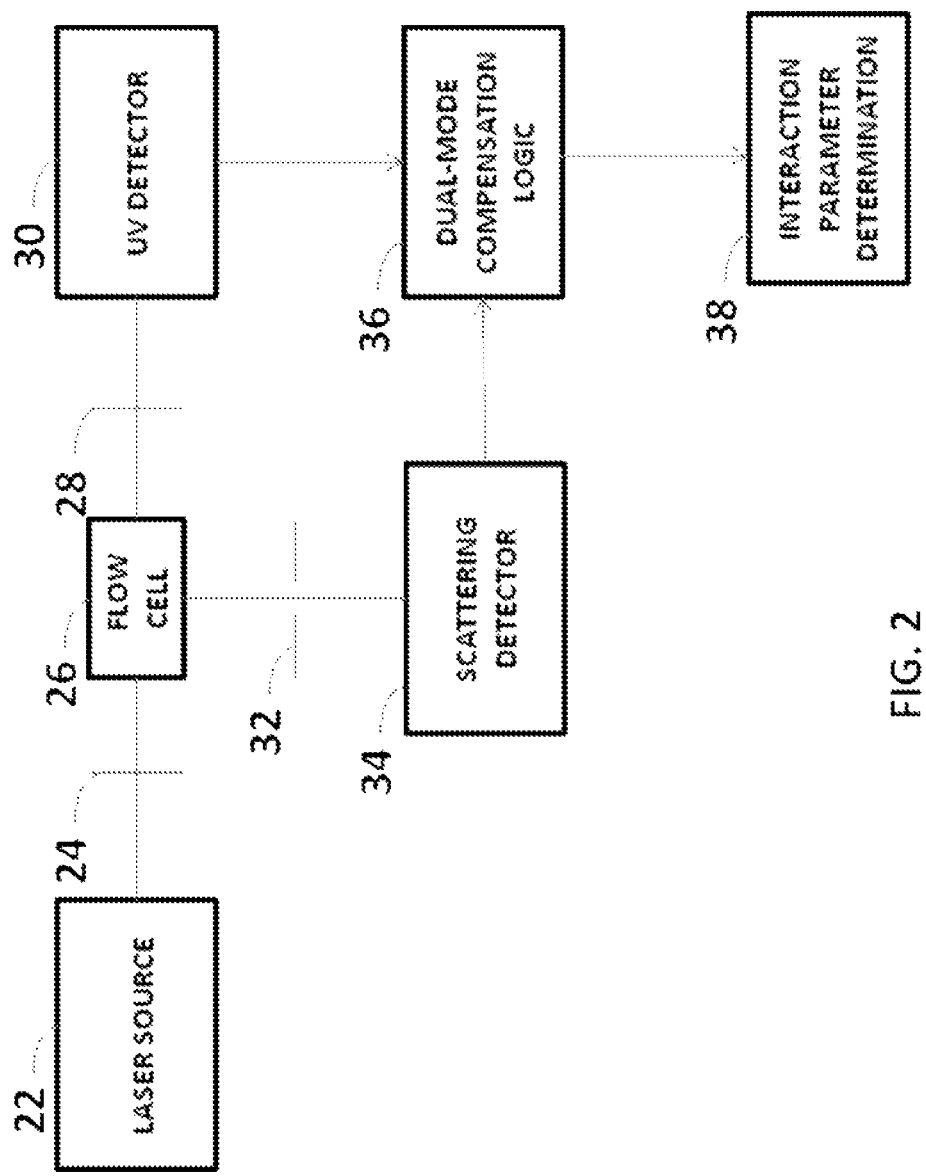
FIG. 2 is a block diagram of an illustrative interaction characterization instrument according to the invention.

Referring to FIG. 1, an illustrative interaction characterization instrument 20 according to the invention 22 includes a LED source that preferably includes a 280 nm light emitting diode. The optical axis of the LED passes through a focusing lens 24 into a flow cell 26. The flow cell preferably has a small cross-section to keep the illuminated sample size small. In this embodiment it is implemented with a square capillary tube with 0.25 mm sides.

Light from the source that is not absorbed or scattered by the sample may additionally pass through a band-pass filter 28 (although this filter should not be required for a narrow-band LED source), such as an interference filter, to a UV detector 30, which can include a low-noise photometer, PIN diode, photomultiplier or other suitable type of detector element. Light from the source that is scattered at a predetermined angle passes through a slit or pinhole 32 and on to a scattering detector 34. The scattering detector and slit are positioned to perform a static light scattering (SLS) particle-size measurements on light scattered at 90 degrees in this embodiment, but other scattering angles including backscattering angles can also be used. Optical fibers can be used in the optical paths in the instrument but they are not necessary and generally not desirable.

Outputs of the UV detector 30 and scattering detector 34 are provided to inputs of a dual-mode compensation module 36. The dual-mode compensation logic corrects the scattering signal output based on the amount of light that reaches the UV detector. The resulting corrected signals are then provided to an interaction parameter determination module 38, which preferably computes a $B_{22}$ parameter. These compensation and parameter determination modules can be implemented together or separately using a general-purpose computer workstation running special-purpose software, dedicated hardware, or a combination of both.

In operation, a slug of a particulate sample, such as a protein or other macromolecule, is injected into a carrier flow that flows through the flow cell 24. As the sample flow passes through the flow cell, the scattering detector and UV detector acquire measured scattering and UV transmission values. The measured values from the two detectors are acquired simultaneously or are at least acquired close in time to each other, relative to the flow rate. In the illustrative embodiment, the flow rate is set to cause a 1-10 microliter slug to pass the detectors in 20 minutes during which they each take 100 measurements. These measurements can be preformed automatically and combined to obtain a $B_{22}$ value for the sample. Formulation buffer exchange could be performed by using conventional liquid chromatography (LC) guard columns (with known low molecular weight cutoff) along with a carrier stream consisting of the formulation buffer of interest, to acquire $B_{22}$ values from a series of different formulations without having to manually prepare the protein sample in each of the formulation buffers of interest. A filter, such as a membrane or frit filter, can also be provided to prevent particles above a predetermined threshold size from affecting the measurement.

The present invention has now been described in connection with a number of specific embodiments thereof. However, numerous modifications which are contemplated as falling within the scope of the present invention should now be apparent to those skilled in the art. For example, a UV filter and/or scattering slit may be added (e.g., if the LED does not have a sufficiently narrow bandwidth). The source can also be a laser diode, or use a different wavelength, such as 220 nm. Therefore, it is intended that the scope of the present invention be limited only by the scope of the claims appended hereto. In addition, the order of presentation of the claims should not be construed to limit the scope of any particular term in the claims.

What is claimed is:
1. A particle interaction characterization instrument, comprising:
    a flow cell for a liquid sample that includes suspended particles,
    a light source positioned to illuminate the suspended particles in the liquid sample fluid in the sample vessel,
    a first scattering detector positioned to receive light from the light source that has been scattered by the particles suspended in sample fluid in the sample vessel at at least one predetermined scattering angle,
    an ultraviolet transmittance detector positioned to receive a portion of the light from the source that passes through the suspended particles without being absorbed or scattered, and interaction analysis logic responsive to both the scattering detector and the ultraviolet detector, and being operative to derive at least one interaction property for the suspended particles.

2. The apparatus of claim 1 wherein the light source is an LED.

3. The apparatus of claim 1 wherein the light source is a 280 nm LED.

4. The apparatus of claim 1 wherein the flow cell has a cross section of 0.5 mm or less.

5. The apparatus of claim 1 wherein the light source is positioned to illuminate the flow cell independent of any optical fiber.

6. The apparatus of claim 1 wherein the interaction analysis logic includes dual-mode compensation logic that is operative to correct a scattering signal from the scattering detector based on an amount of light that reaches the ultraviolet detector.

7. The apparatus of claim 1 wherein the interaction analysis logic is operative to derive a $B_{22}$ value for the sample.

8. The apparatus of claim 1 wherein the instrument is operative to automatically perform a succession of simultaneous ultraviolet and scattering measurements.

9. A particle interaction characterization method, including the steps of:
    illuminating particles suspended in a sample fluid with a light source,
    detecting light from the step of illuminating that has been scattered by the particles,
    detecting ultraviolet light from the step of illuminating that passes through the sample without being absorbed or scattered, and
    deriving at least one interaction property for the suspended particles based on both results of the step of detecting scattered light and results of the step of detecting ultraviolet light.

10. The method of claim 9 wherein the step of detecting scattered light and the step of detecting ultraviolet light are performed simultaneously during the step of illuminating.

11. The method of claim 9 further including the step of correcting a scattering signal from the step of detecting scattered light based on an amount of light that reaches the ultraviolet detector.

12. A particle interaction characterization instrument, comprising:
    means for illuminating particles suspended in a sample fluid,
    means for detecting light from the means for illuminating that has been scattered by the particles,
    means for detecting ultraviolet light from the means for illuminating that passes through the sample without being absorbed or scattered, and
    means for deriving at least one interaction property for the sample based on both signals from the means for detecting scattered light and signals from the means for detecting ultraviolet light.

13. The method of claim 9 wherein the sample is a dilute protein sample.

* * * * *